United States Patent [19]
Yeary

[11] Patent Number: 5,223,101
[45] Date of Patent: Jun. 29, 1993

[54] LOW COLOR, LOW TURBIDITY SULFOLANE

[75] Inventor: David L. Yeary, Borger, Tex.

[73] Assignee: Phillips Petroleum Company, Bartlesville, Okla.

[21] Appl. No.: 658,822

[22] Filed: Feb. 22, 1991

[51] Int. Cl.$^5$ .............................................. B01D 3/10
[52] U.S. Cl. ........................................ 203/4; 203/75; 203/77; 203/78; 203/80; 549/87
[58] Field of Search .................... 203/4, 75, 77, 78, 80; 549/87

[56] References Cited

U.S. PATENT DOCUMENTS

| | | | |
|---|---|---|---|
| 3,252,997 | 5/1966 | Ridderikhoff et al. | 549/87 |
| 3,352,765 | 11/1967 | Warner et al. | 203/70 |
| 3,514,469 | 5/1970 | Phillips et al. | 549/87 |
| 4,383,895 | 5/1983 | Ernst et al. | 203/91 |
| 4,861,447 | 8/1989 | Blytas et al. | 204/181.8 |

FOREIGN PATENT DOCUMENTS

| | | | |
|---|---|---|---|
| 1254639 | 11/1967 | Fed. Rep. of Germany | 549/87 |
| 287244 | 2/1965 | Netherlands | 549/87 |
| 0329181 | 3/1972 | U.S.S.R. | 549/87 |
| 2194238 | 3/1988 | United Kingdom | 549/87 |

OTHER PUBLICATIONS

Kirk-Othmer Encyclopedia of Chemical Technology, vol. 21, pp. 961-968.

Primary Examiner—Virginia Manoharan
Attorney, Agent, or Firm—George E. Bogatie

[57] ABSTRACT

Purification of crude sulfolane to remove color imparting and turbidity imparting impurities therefrom is achieved by a two-pass distillation process wherein purified sulfolane is withdrawn from the bottom of a column in the second distillation pass.

4 Claims, 2 Drawing Sheets

LOW COLOR, LOW TURBIDITY SULFOLANE

This invention relates to a process for refining crude sulfolane. In one aspect, it relates to a plural distillation process for refining crude sulfolane. In another aspect, it relates to a process for producing sulfolane having a low-color content and further having low-turbidity.

BACKGROUND OF THE INVENTION

Sulfolane is a compound which is used principally as a solvent for extraction of benzene, toluene and xylene from mixtures with aliphatic hydrocarbons. Sulfolanes are also useful for a variety of other purposes, such as pesticidal compositions, textile applications, polymer solvent, acid gas treating, intermediates in the production of other organic chemicals, and solvents for various hydrocarbons, fatty acids, or fatty acid esters.

Because of its high dielectric constant, low volatility, and solubilizing characteristics, sulfolane is also useful for a wide variety of electronic and electrical applications, e.g. as a coil insulating component, battery solute, capacitor impregnate, and solvent in electroplating baths.

The production of sulfolane is well known by those familiar in the art and is disclosed in numerous references, such as U.S. Pat. No. 3,514,469, issued to J. E. Phillips et al., which patent is incorporated herein by reference. Crude sulfolanes are generally prepared by reacting sulfur dioxide with a sulfolene precursor to form a sulfolene. The resulting sulfolene is then catalytically hydrogenated to form the sulfolane. In its pure state, sulfolane is a colorless, highly polar, water soluble compound. Crude, or so called technical grade, sulfolane compound widely produced for use in extractive distillations, however, generally contains small amounts of impurities, such as insoluble sulfones, polymeric substances and other conversion products, which impart light brown color and turbidity to the crude sulfolane.

Recent interest in preparing low-color, low-turbidity sulfolane comes from new uses of sulfolane in electrical or electronic applications, such as preparing compositions for cleaning electronic circuit boards. In preparing compositions for cleaning electronic circuit boards, color and turbidity characteristics of the sulfolane used in the preparation of the circuit board cleaning compound are extremely important.

Accordingly, it is an object to this invention to provide a convenient process for the purification of crude sulfolane.

It is another object of this invention to provide a process which is safe, effective, simple and economical.

It is another object of this invention to recover liquid sulfolane having low-color and low-turbidity characteristics.

SUMMARY OF THE INVENTION

In accordance with the present invention, I have discovered that purified sulfolane having desirable color and turbidity characteristics can be provided in a very simple manner in two-pass distillation process. The first pass distillation of crude sulfolane, containing color and turbidity imparting impurities, provides an overhead material having desirable color characteristics, but having high turbidity. In the second distillation pass, the overhead product of the first pass is distilled with a bottoms product from the second pass, providing a material having desirable charateristics for both color and turbidity.

In a preferred embodiment, the initial distillation is carried out in a column under vacuum conditions, with the overhead distillate product passed to a vessel for temporary storage, and the bottoms product recycled to the feed of the distillation column. In the second pass distillation, which is also carried out in a column under vacuum conditions, the initial distillate is redistilled, so as to produce a bottoms material having desirable characteristics for both color and turbidity, and which is the desired purified sulfolane produced in accordance with the process of this invention.

Further aspects and additional advantages of the invention will be apparent from the following detailed description of the preferred embodiment of the invention, as illustrated by the drawings in which:

DETAILED DESCRIPTION OF THE PREFERRED EMBODIMENT

Figure 1:
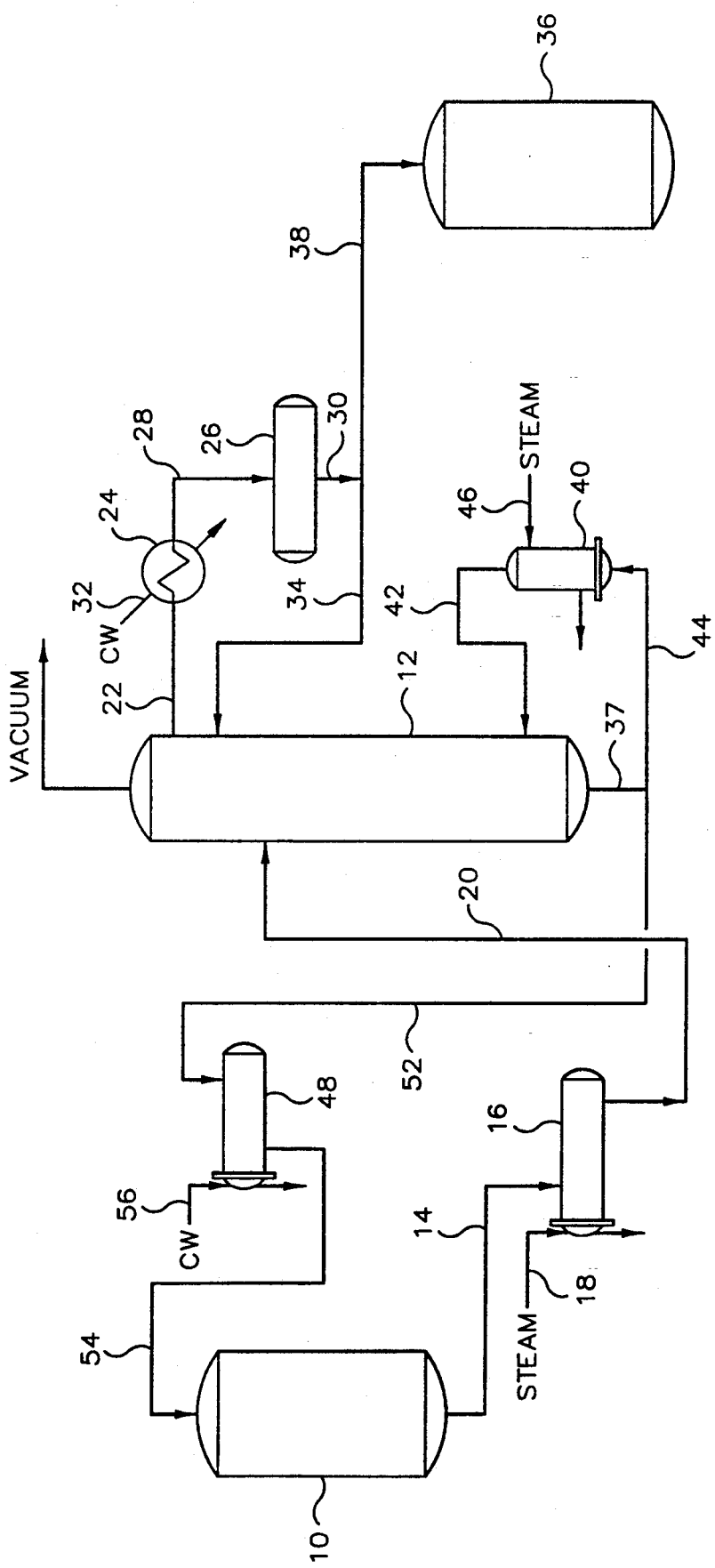
FIG. 1 is a simplified schematic diagram illustrating process flow of the first pass distillation according to this invention.
Figure 2:
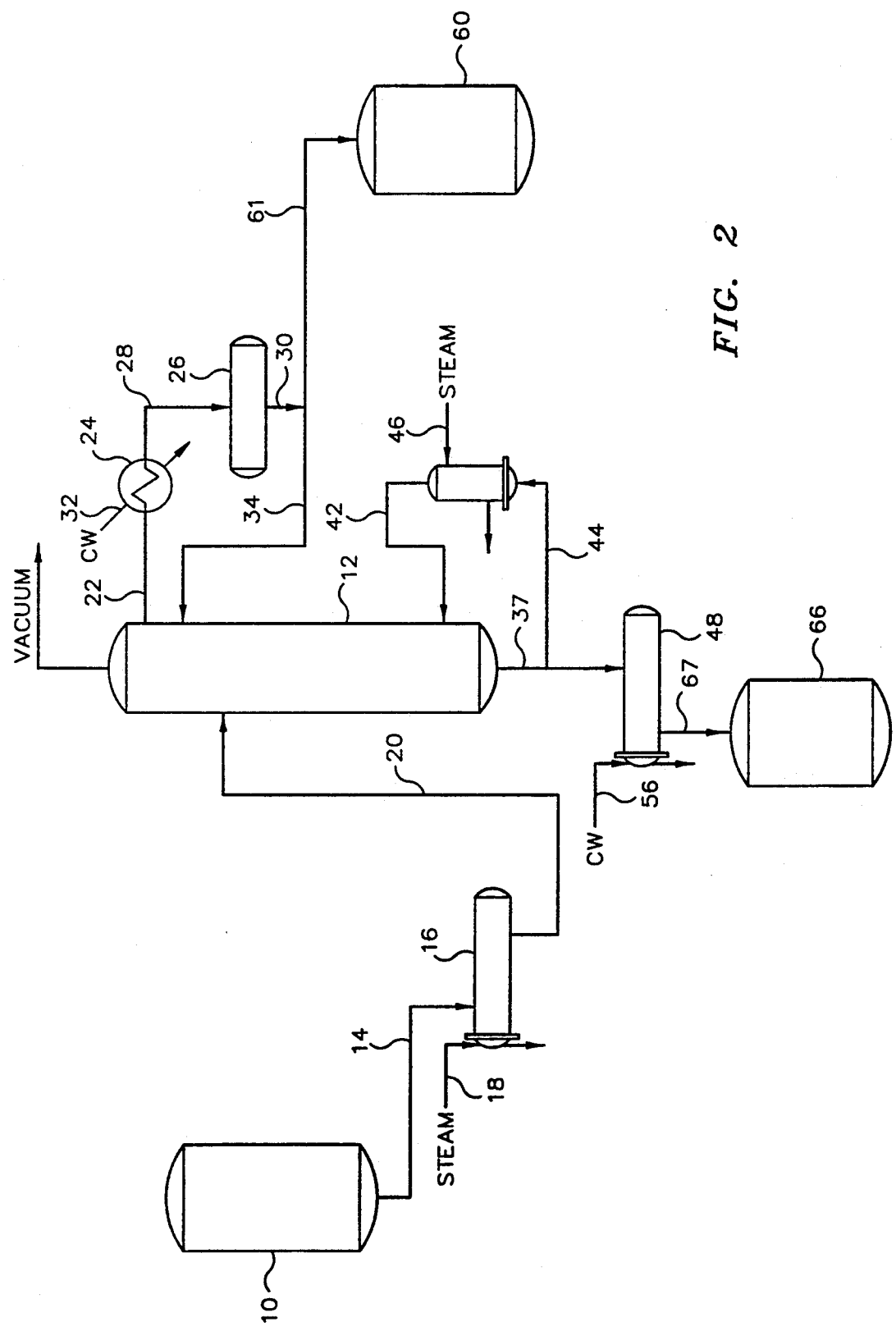
FIG. 2 is a simplified schematic diagram illustrating process flow of the second pass distillation according to this invention.

It will be appreciated by those skilled in the art that since FIG. 1 and FIG. 2 are schematic only, many items of equipment which would be needed for successful operation of a commercial plant have been omitted for the sake of clarity. Such items of equipment would include for example, temperature flow and pressure measurement instruments with corresponding process controllers, pumps, compressors, additional heat exchangers, valves etc. All these items would be provided in accordance with standard chemical engineering practice to maintain desired conditions throughout the process and are not necessary to describe the present invention. It should also be understood that the representative temperatures and pressures set forth herein, with relation to the description to the drawings and the example, are illustrative only and are not to be considered as limiting.

The sulfolane compounds which may be purified according to the process of this invention include sulfolane and its homologs. The present invention is particularly applicable for purifying crude sulfolane. As used herein "crude sulfolane" is a product prepared by reacting sulfur dioxide with a suitable conjugated diolefin, such as butadiene, isoprene, etc. and hydrogenating the resulting sulfolene compound to a corresponding sulfolane compound. The crude sulfolane so produced generally contains a number of impurities, such as ethers and polymeric substances, in addition to a certain concentration of unconverted sulfolene. It is presumably the presence of these impurities which impart undesirable color and turbidity characteristics to the crude sulfolane.

Referring now to FIG. 1, there is illustrated the first pass distillation according to the present invention. The process begins with crude sulfolane stored in a feed tank 10. The crude sulfolane is passed via conduit 14 to a preheater 16, where the crude sulfolane feed is heated by heat exchange with high pressure steam supplied to preheater 16 via conduit 18. The crude sulfolane is preheated to a temperature of about 164° F. in preheater 16 and is then passed to the central portion of distillation column 12 via conduit 20. The distillation column 12 can be any suitable column for purifying volatile materials which is adapted for operating under vacuum conditions. The crude sulfolane is distilled in column 12 and an overhead sulfolane vapor stream is withdrawn from the column 12 through conduit 22 and condensed in condenser 24. The condenser 24 is provided with a cooling medium flow through conduit 32. The thus condensed liquid stream flowing through condenser 24 is provided to the overhead accumulator 26 through conduit 28. Liquid is withdrawn from accumulator 26 through conduit 30. A portion of the liquid flowing in conduit 30 is provided as an upper external reflux to distillation column 12 through the combinations of conduits 30 and 34. The remaining portion of the liquid flowing through conduit 30 is provided through conduit 38 to a storage vessel 36, where it is retained as an intermediate product which is temporarily stored in vessel 36.

A liquid stream is also withdrawn from the bottom of distillation column 12 through conduit 37 and a portion of the thus withdrawn liquid is passed through heat exchanger 40 via conduit 44 and then returned to the lower portion of distillation column 12 through conduit 42. Heat is supplied to the liquid stream flowing through conduit 44 by the high pressure stream supplied to the heat exchanger 40 through conduit 46. The remaining portion of liquid withdrawn from the bottom of distillation column 12 through conduit 37 is passed through heat exchanger 48 and, if desired, cooled in heat exchanger 48, and then returned to the storage feed tank 10 through conduit 54. Heat exchanger 48 is provided with a cooling medium flow through conduit 56.

In the presently illustrated embodiment, a batch-type process is preferred wherein the distillation of column 12 is flushed of colored and turbid material on completion of the first pass distillation and the second distillation pass is carried out in the same column as the first pass. If desired, however, a second distillation column could be employed for use in the second distillation pass.

Referring now to process flow illustrated in FIG. 2, it is noted that the units employed in the process illustrated in FIG. 2 operate in the same manner as the corresponding units illustrated in FIG. 1, and further the process flow differs only slightly from that of FIG. 1. Accordingly, reference numerals used in FIG. 1 are used for corresponding units in FIG. 2. Differences between FIG. 1 and FIG. 2 are primarily in the operating conditions employed in the distillation, which will be set forth in an example herein below, and in the disposition of the material withdrawn from the distillation column 12. Referring now specifically to FIG. 2, the portion of the liquid withdrawn from accumulator 26 through conduit 30, which remains after supplying external reflux to column 12 through conduit 34, is passed to vessel 60 through conduit 61. The liquid supplied to vessel 60 is considered waste material and is disposed of in any suitable manner. Still referring specifically to FIG. 2, purified sulfolane is withdrawn from heat exchanger 48 through conduit 67 and is supplied to storage vessel 66 for subsequent use in any desired application, such as a component for forming a compound for cleaning electronic circuit boards.

In accordance with the process of this invention sulfolane, which is withdrawn from the bottoms of the second distillation pass, has a color in the range of from about 20 to about 120 APHA and a turbidity in the range of from about 0.5 to about 5 JCU, and preferably the purified sulfolane color will be a range of from about 30 to about 80 APHA and the turbidity will be in a range of from about 1 to about 2 JCU.

In general accurate color measurements of liquid samples of the purified sulfolane from the bottoms liquid which collects during the second distillation pass in column 12 can be made in accordance with industrial and process standards involving color matching. In using color matching standards the color standard is compared with the sample material with the assistance of a spectrophotometer. Several color standards are used in process industries. In accordance with this invention, however, the American Public Health Association (APHA) color scale is utilized for determining the acceptability of the color of the purified sulfolane. As used herein, the term "low-color" is taken to mean a color corresponding to APHA 100 or less. Color analysis instruments in which color is determined by ASTM D-1209 are available from a variety of commercial suppliers.

The turbidity of a fluid is a measure of the amount of solids in suspension. Instruments, generally commercially available, use a standard scale called JCU. As used herein, the "low-turbidity" is taken to mean a turbidity of 5 JCU or lower. A model 2100A instrument available from Hach Chemical Co. Loveland, Colo. is preferred for turbidity measurements.

The following examples illustrate a commercial process for purifying sulfolane and are presented in further illustration of the present invention and are not to be considered as unduly limiting this invention.

EXAMPLE 1

A commercial size distillation column was employed to distill about 9,000 gallons of crude sulfolane. Table 1 below sets forth typical operating flow rates and temperatures associated with the distillation column and auxiliary equipment illustrated in FIG. 1. The distillation column was operated under vacuum conditions of 1.0 mm Hg. Distillation of crude sulfolane under these conditions resulted in a low-color sulfolane overhead product, which was collected in vessel 36. The low-color sulfolane collected in vessel 36 had a color of about 15 APHA.

TABLE 1

| | First Pass Distillation | |
|---|---|---|
| Part Illustrated | Flow (gpm) | Temp. (°F.) |
| 10 | 6.0 | 164 |
| 12 | — | 274* |
| 18 | 0.0 | — |
| 20 | 6.0 | 164 |
| 22 | — | 252 |
| 34 | 0.4 | |
| 36 | — | — |
| 38 | 3.0 | — |
| 40 | — | 297 |
| 46 | 1000 | — |

*Central portion of column 12

EXAMPLE 2

The distillation column employed in Example 1 was flushed with 300–400 gallons of the low-color sulfolane produced in Example 1 to remove residual crude sulfolane out of the lower portion and the reboiler of the distillation column. The overhead product obtained in Example 1 was then distilled in a second pass through the distillation column. Table 2 below sets forth typical operating flow rates and temperatures associated with the distillation column and auxiliary equipment illustrated in FIG. 2. The distillation column was operated under vacuum conditions of 0.5 mm Hg. Distillation of the overhead product of the first pass distillation under these conditions resulted in a low-color but highly turbed overhead product, which was discarded, and sulfolane having both low-color and low-turbidity which accumulated in the lower portion of the distillation column in the second pass distillation and which was withdrawn from the column 12 and collected in vessel 66. The low-color, low-turbidity sulfolane, thus collected in vessel 66, had a color of about 70 APHA and a turbidity of about 1.5 JCU.

TABLE 2

| Second Pass Distillation | | |
| --- | --- | --- |
| Part Illustrated | Flow (gpm) | Temp. (°F.) |
| 10 | 3.0 | 192 |
| 12 | — | 257* |
| 18 | 0.0 | — |
| 20 | 3.0 | 192 |
| 22 | — | 208 |
| 34 | 2.8 | — |
| 40 | — | 275 |
| 46 | 500 | — |
| 61 | 0.4 | — |

*Central portion of column 12.

It is to be understood that reasonable variations and modifications of conditions are possible by those skilled in the art, and such modifications and variations are within the scope of the described invention in the appended claims.

That which is claimed:

1. A process for purifying a crude sulfolane containing impurities which impart color and additional impurities which impart turbidity to said crude sulfolane, so as to provide a purified sulfolane, having low-color and low-turbidity, said process comprising the following steps performed in the sequence set forth:
    (a) distilling said crude sulfolane in a first distillation column operated under vacuum conditions of about 1 mm of mercury to produce an overhead material, having a reduced concentration of said color imparting impurities, and an increased concentration of said turbidity imparting impurities compared to the concentration of the corresponding impurities contained in said crude sulfolane;
    (b) distilling said overhead material obtained in step (a) in a second distillation column operated under vacuum conditions of about 0.5 mm of mercury to produce a bottoms material having a reduced concentration of said turbidity imparting impurities compared to the concentration of said turbidity imparting impurities contained in said overhead material; and
    (c) withdrawing said purified sulfolane having a color of from about 20 to about 120 APHA and a turbidity of from about 0.5 to about 5 JCU from the bottom portion of said second distillation column.

2. A process in accordance with claim 1 wherein an external liquid reflux is provided to said first distillation column and said second distillation column, and wherein said liquid reflux is provided in greater amount to said second distillation column compared to said first distillation column.

3. A process in accordance with claim 2 wherein said crude sulfolane is supplied to said first distillation column from a feed tank, and wherein said process additionally comprises the following steps:
    (a) withdrawing material which accumulates in the bottom of said first distillation column; and
    (b) recycling said withdrawn bottoms material of said first distillation column to said feed tank.

4. A process in accordance with claim 3, wherein the same column is utilized for said first distillation column and said second distillation column, said process additionally comprising the following step preformed between steps (a) and step (b):
    flushing residual color material out of said first distillation column.

* * * * *